(12) United States Patent
Dos Santos et al.

(10) Patent No.: US 10,398,312 B2
(45) Date of Patent: Sep. 3, 2019

(54) FREQUENCY-BASED MODE MIXING FOR SURGICAL LASER ILLUMINATION

(71) Applicant: Novartis AG, Basel (CH)

(72) Inventors: Cesario Dos Santos, Newport Beach, CA (US); Gerald David Bacher, Carlsbad, CA (US); Ronald Smith, Irvine, CA (US); Alireza Mirsepassi, Irvine, CA (US); Michael Papac, North Tustin, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/882,888

(22) Filed: Jan. 29, 2018

(65) Prior Publication Data

US 2018/0214021 A1 Aug. 2, 2018

Related U.S. Application Data

(60) Provisional application No. 62/453,735, filed on Feb. 2, 2017.

(51) Int. Cl.
| | |
|---|---|
| *A61B 3/13* | (2006.01) |
| *A61B 3/00* | (2006.01) |
| *G02B 21/06* | (2006.01) |
| *A61B 90/30* | (2016.01) |
| *G02B 21/00* | (2006.01) |
| *H01S 3/00* | (2006.01) |

(52) U.S. Cl.
CPC .............. *A61B 3/13* (2013.01); *A61B 3/0008* (2013.01); *A61B 90/30* (2016.02); *G02B 21/0012* (2013.01); *G02B 21/06* (2013.01); *A61B 2090/306* (2016.02); *H01S 3/005* (2013.01); *H01S 3/0057* (2013.01); *H01S 3/0085* (2013.01)

(58) Field of Classification Search
CPC .......... A61B 3/0008; A61B 3/14; A61B 3/12; A61B 3/102; A61B 3/0025
USPC ....................................................... 351/221
See application file for complete search history.

(56) References Cited

U.S. PATENT DOCUMENTS

| | | | |
|---|---|---|---|
| 5,395,362 A | 3/1995 | Sacharoff et al. | |
| 6,299,307 B1* | 10/2001 | Oltean | A61B 3/113 |
| | | | 351/210 |
| 7,444,057 B2 | 10/2008 | Dacquay et al. | |
| 7,499,624 B2 | 3/2009 | Dacquay et al. | |
| 10,238,543 B2 | 3/2019 | Farley | |
| 2003/0001071 A1 | 1/2003 | Mandella et al. | |
| 2003/0229270 A1 | 12/2003 | Suzuki et al. | |
| 2004/0126048 A1 | 7/2004 | Dave et al. | |
| 2004/0151008 A1 | 8/2004 | Artsyukhovich et al. | |
| 2005/0027288 A1 | 2/2005 | Oyagi et al. | |
| 2007/0047059 A1 | 3/2007 | Howard et al. | |
| 2008/0144148 A1 | 6/2008 | Kusunose et al. | |
| 2008/0246919 A1 | 10/2008 | Smith | |

(Continued)

FOREIGN PATENT DOCUMENTS

| | | |
|---|---|---|
| CN | 103799961 A | 5/2014 |
| GB | 2467181 A | 7/2010 |

(Continued)

*Primary Examiner* — Mohammed A Hasan

(57) ABSTRACT

Frequency-based mode mixing may be used to homogenize different modes in an optical fiber used for surgical illumination. A laser modulator may introduce frequency modulation to laser light to generate a homogeneous illumination field due to increased mode mixing in the optical fiber.

16 Claims, 5 Drawing Sheets

(56) References Cited

U.S. PATENT DOCUMENTS

| | | |
|---|---|---|
| 2008/0269731 A1* | 10/2008 | Swinger ............. A61F 9/00806 606/5 |
| 2009/0059359 A1 | 3/2009 | Nahm et al. |
| 2010/0157622 A1 | 6/2010 | Stocks |
| 2011/0144745 A1 | 6/2011 | Martin et al. |
| 2012/0203075 A1 | 8/2012 | Horvath et al. |
| 2013/0144278 A1 | 6/2013 | Papac et al. |
| 2013/0150839 A1 | 6/2013 | Smith et al. |
| 2013/0158392 A1 | 6/2013 | Papac et al. |
| 2013/0158393 A1 | 6/2013 | Papac et al. |
| 2013/0338648 A1* | 12/2013 | Hanebuchi ............. A61F 9/008 606/4 |
| 2014/0333978 A1 | 11/2014 | Hereen et al. |
| 2014/0350368 A1 | 11/2014 | Irisawa |
| 2015/0366443 A1 | 12/2015 | Liolios et al. |
| 2018/0214018 A1 | 8/2018 | Dos Santos et al. |
| 2018/0214021 A1 | 8/2018 | Dos Santos et al. |
| 2018/0214237 A1 | 8/2018 | Dos Santos et al. |
| 2018/0214238 A1 | 8/2018 | Dos Santos et al. |
| 2018/0214239 A1 | 8/2018 | Dos Santos et al. |

FOREIGN PATENT DOCUMENTS

| | | |
|---|---|---|
| KR | 20110011052 A | 2/2011 |
| WO | 9314432 A2 | 7/1993 |
| WO | 2015130651 A1 | 9/2015 |

\* cited by examiner

FREQUENCY-BASED MODE MIXING FOR SURGICAL LASER ILLUMINATION

BACKGROUND

Field of the Disclosure

The present disclosure relates to surgical illumination, and more specifically, to frequency-based mode mixing for surgical laser illumination.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

Additionally, an illumination source is typically introduced into the fundus to illuminate the area where the surgeon will be working. The illumination source is typically implemented as a surgical tool having an illuminator assembly that also penetrates the sclera and may be combined with other surgical tools. The use of optical fibers transmitting coherent light as illumination sources for surgery is desirable because of the high light intensity provided within very small physical dimensions available with optical fibers.

SUMMARY

The disclosed embodiments of the present disclosure provide for frequency-based mode mixing may be used to homogenize different modes in an optical fiber used for surgical illumination. A laser modulator may introduce frequency modulation to laser light to generate a homogeneous illumination field due to increased mode mixing in the optical fiber.

In one aspect, a disclosed method is for surgical illumination. The method may include projecting first light having a first frequency from a coherent light source onto a laser modulator, and controlling the laser modulator to modulate the first frequency of the first light to generate second light, the first light used for illumination of a patient during a surgery. The method may also include projecting the second light onto an optical fiber, and transmitting the second light from the optical fiber to a second optical fiber that projects the second light onto the patient.

In any of the disclosed embodiments of the method, the surgery may be an ophthalmic surgery, and the second optical fiber may project the second light into an eye of the patient.

In any of the disclosed embodiments, the method operation of controlling the laser modulator may further include controlling a modulation amplitude to modulate the first frequency of the first light.

In any of the disclosed embodiments, the method operation of controlling the laser modulator may further include controlling the modulation amplitude based on a transmission characteristic of the optical fiber.

In any of the disclosed embodiments of the method, the transmission characteristic of the optical fiber may be selected from at least one of: a length of the optical fiber, a dispersion value for the optical fiber, a core diameter of a core of the optical fiber, and an index of refraction of the core of the optical fiber.

In any of the disclosed embodiments of the method, the coherent light source may be a monochromatic laser.

In any of the disclosed embodiments of the method, projecting the second light onto the optical fiber may further include projecting the second light onto the optical fiber using a condenser lens.

In any of the disclosed embodiments of the method, a modulation frequency to modulate the first frequency of the first light may be at least 30 Hz.

In any of the disclosed embodiments of the method, the coherent light source may be a third optical fiber receiving the first light from a laser, while the laser modulator is included in a laser modulator device that may further include an input optical connector for connection to the third optical fiber, an output optical connector for connection to the optical fiber, and a power source to power the laser modulator.

In a further aspect, a disclosed device is for surgical illumination. The device may include a coherent light source for generating first light having a first frequency for illumination of a patient during a surgery, a laser modulator for receiving the first light and for modulating the first frequency of the first light to generate second light, an optical fiber for receiving the second light, and a second optical fiber receiving the second light from the optical fiber, the second optical fiber projecting the second light onto the patient.

In any of the disclosed embodiments of the device, the surgery may be an ophthalmic surgery, and the second optical fiber may project the second light into an eye of the patient.

In any of the disclosed embodiments of the device, the laser modulator may be controlled by controlling a modulation amplitude to modulate the first frequency of the first light.

In any of the disclosed embodiments of the device, the laser modulator may be controlled by controlling the modulation amplitude based on a transmission characteristic of the optical fiber.

In any of the disclosed embodiments of the device, the transmission characteristic of the optical fiber may be selected from at least one of: a length of the optical fiber, a dispersion value for the optical fiber, a core diameter of a core of the optical fiber, and an index of refraction of the core of the optical fiber.

In any of the disclosed embodiments of the device, the coherent light source may be a monochromatic laser.

In any of the disclosed embodiments, the device may further include a condenser lens for projecting the second light onto the optical fiber.

In any of the disclosed embodiments of the device, a modulation frequency to modulate the first frequency of the first light may be at least 30 Hz.

In any of the disclosed embodiments of the device, the coherent light source may be a third optical fiber receiving the first light from a laser, while the laser modulator may be included in a laser modulator device that may further include an input optical connector for connection to the third optical fiber, an output optical connector for connection to the optical fiber, and a power source to power the laser modulator.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
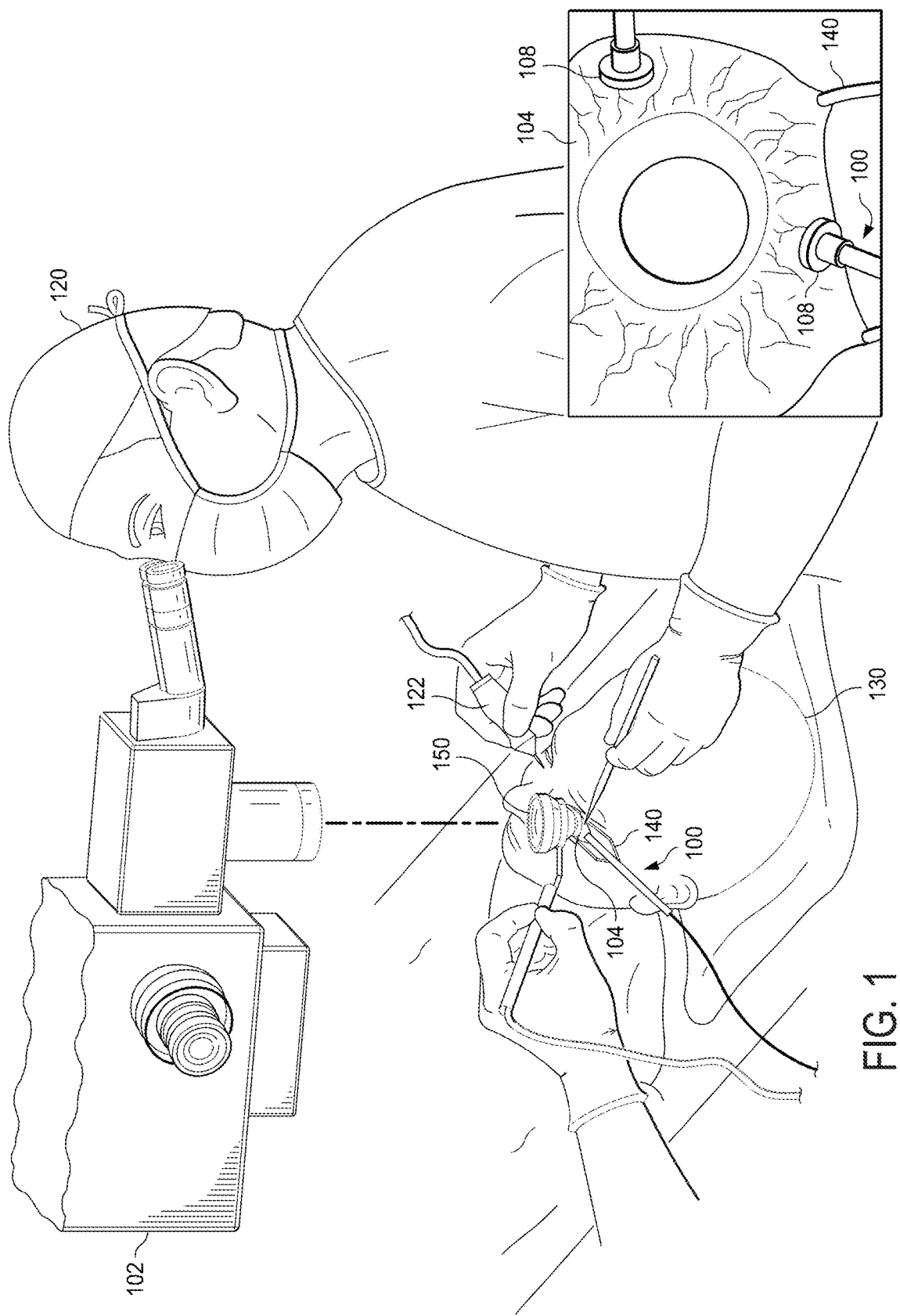
FIG. 1 is a depiction of an embodiment of an ophthalmic surgery using a surgical microscope and a surgical tool with an illuminator assembly.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, the use of optical fibers and coherent light sources is desirable for surgical illumination because of the high light intensity provided within the very small physical dimensions of an optical fiber. Although such surgical illumination sources may be used in various medical and surgical applications, one exemplary application is in eye surgery, such as for vitreoretinal surgery.

For vitreoretinal surgery, for example, the illumination source is typically implemented as a surgical tool having an illuminator assembly that penetrates the sclera and may be combined with other surgical tools. At a distal end of the illuminator assembly, a very small diameter optical fiber may be used to project light into the fundus to illuminate surgical procedures performed within the eye. The very small diameter fiber, for example having a fiber core of about 25-100 µm, is typically coupled to an optical fiber that couples proximally to a coherent light source, such as a laser source. Although various types of optical fibers may be used, multi-mode optical fibers may be used to transmit coherent light into the eye for illumination.

However, as coherent light is transmitted through a multi-mode optical fiber, different groups of photons of the coherent light, referred to as "modes", within the fiber may traverse slightly different path lengths. As a result of the different path lengths experienced by different modes within the optical fiber, the modes may constructively and destructively interfere with each other during propagation within the optical fiber. As the different modes exit the optical fiber from a fiber core, an illumination field provided by the exiting light may appear inhomogeneous due to the inter-mode interference. The inter-mode interference may be highly sensitive to temperature, fiber strain, fiber motion, and may generally become quite noticeable to the human eye, since the inhomogeneous illumination field projects an undesired dynamic pattern, instead of a homogeneous illumination field projecting uniform background light. Because the inhomogeneous illumination field appears as different regions of different colored light that may be dynamic, the inhomogeneous illumination field may be poorly suited for surgical illumination.

For example, in vitreoretinal surgery, a clear and unambiguous view of various fine biostructures in the eye is highly desirable to enable a surgeon to operate safely and effectively, which the inhomogeneous illumination field may not provide. In particular, the inhomogeneous illumination field is observed with monochromatic laser sources, or combinations of monochromatic laser sources in some implementations. The monochromatic laser sources may exhibit fewer modes and, thus, a lesser degree of mode mixing within the optical fiber that enables homogenization of the coherent light into a desired homogeneous illumination field. Furthermore, as various surgical tools are designed and implemented, such as endoilluminators or surgical tools with combined illumination, the use of smaller fiber diameters carrying high light intensity becomes increasingly desirable. However, the inter-mode interference issues become increasingly exacerbated as the size (i.e., diameter) of an optical fiber decreases, which may undesirably constrain the use of such compact illumination systems. Also, in surgical illumination applications, a relatively short length of optical fiber is used, such as about 2-3 m in length. Because mode mixing that leads to a more homogeneous illumination field increases with fiber length, shorter optical fibers used in in surgical illumination applications may experience insufficient mode mixing that results in the inhomogeneous illumination field. Also, optical fibers comprised of a glass core may exhibit fewer modes and less mode mixing, and may be particularly subject to the inhomogeneous illumination field.

As will be described in further detail, frequency-based mixed mode surgical laser illumination is disclosed. The frequency-based mixed mode surgical laser illumination disclosed herein may provide a homogeneous illumination field for surgical illumination using optical fibers to transmit coherent light. The frequency-based mixed mode surgical laser illumination disclosed herein may be used with relatively short and relatively small diameter optical fibers. The frequency-based mixed mode surgical laser illumination disclosed herein may be used with optical fibers having a glass core. The frequency-based mixed mode surgical laser illumination disclosed herein may be implemented at a light source for surgical illumination. The frequency-based mixed mode surgical laser illumination disclosed herein may be implemented as an optical device that can be coupled to an optical fiber providing surgical illumination from a coherent light source. The frequency-based mixed mode surgical laser illumination disclosed herein may be used for illumination of a patient's eye during ophthalmic surgery, such as vitreoretinal surgery.

One manner in which an illumination assembly 100 may be used is illustrated in FIG. 1, in which a surgeon 120 is performing an ophthalmic surgery on an eye 104 of a patient 130 using a surgical tool 122. In FIG. 1, the eye 104 has been exposed using a speculum 140 and a contact lens 150 is held in place on the eye 104 and visually aligned with a surgical microscope 102 to facilitate visualization of inner structures of the eye 104. The surgeon 120 is using the surgical tool 122 to perform surgery on inner structures of the eye 104.

For example, when the surgical tool 122 is a vitrectomy probe, then the surgeon 120 may be using the surgical tool 122 to remove the clear, gel-like vitreous that normally fills the interior of the eye 104, taking care to remove substantially only the vitreous, while avoiding interaction with nearby eye structures, such as the retina, that are extremely sensitive to any mechanical action. The ability of the surgeon to clearly view the fundus is facilitated by a homogenous illumination field that is provided by illumination assembly 100. It is noted that surgical tool 122 may by any of a variety of handheld surgical tools. In some embodiments, illumination assembly 100 may be integrated within surgical tool 122 to provide illumination without having to use a secondary illumination tool.

In the inset of FIG. 1, additional details of the eye 104 during surgery are shown. Two scleral ports 108 for providing cannulated scleral penetration are visible, one for surgical tool 122 and one for illuminator assembly 100. As shown, illuminator assembly 100 may include frequency-based mixed mode surgical laser illumination, as described in further detail below. Accordingly, illuminator assembly 100 may be used to project coherent light into the eye 104 using an optical fiber to transmit the light to project a homogenous illumination field (not visible in FIG. 1) into the fundus.

Modifications, additions, or omissions may be made to illuminator assembly 100 without departing from the scope of the disclosure. The components and elements of surgical illuminator assembly 100, as described herein, may be integrated or separated according to particular applications. Illuminator assembly 100 may be implemented using more, fewer, or different components in some embodiments.

Figure 2:
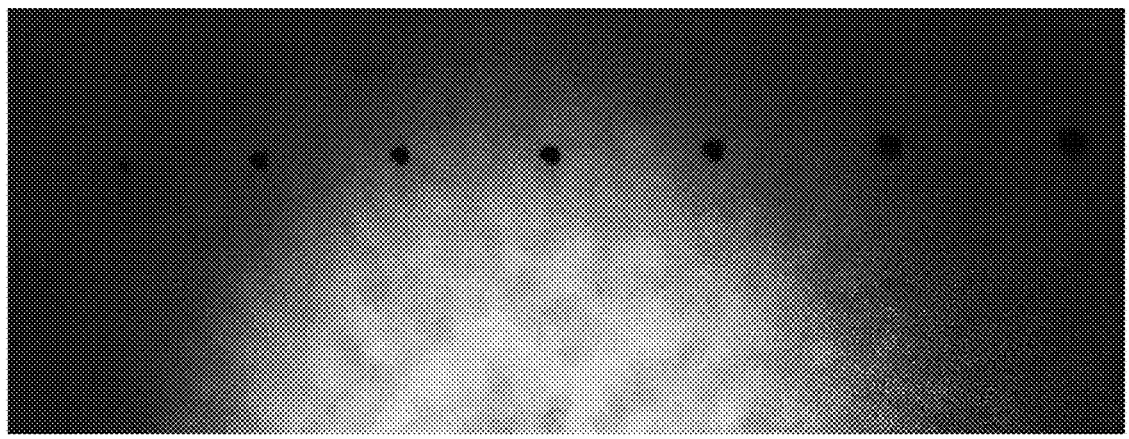
FIG. 2 is an image of inhomogeneous light from fiber modes.

FIG. 2 illustrates an image 200 of inhomogeneous light from fiber modes. Image 200 depicts coherent light from an optical fiber projected onto a screen that is oriented oblique to the page. In image 200, the depicted screen has extraneous annotations written in black ink above and below an inhomogeneous illumination field. The inhomogeneous illumination field in image 200 results from insufficient mode mixing within the optical fiber. The inhomogeneous illumination field in image 200 may exhibit intensity variations up to about 500%, which may be dynamic in many applications and usage scenarios, which is undesirable for surgical illumination, as explained previously. The inhomogeneous illumination field in image 200 may be immediately converted into a homogeneous illumination field, such as a substantially uniform intensity illumination field (not shown) by applying the techniques for mode mixing disclosed herein.

Figure 3:
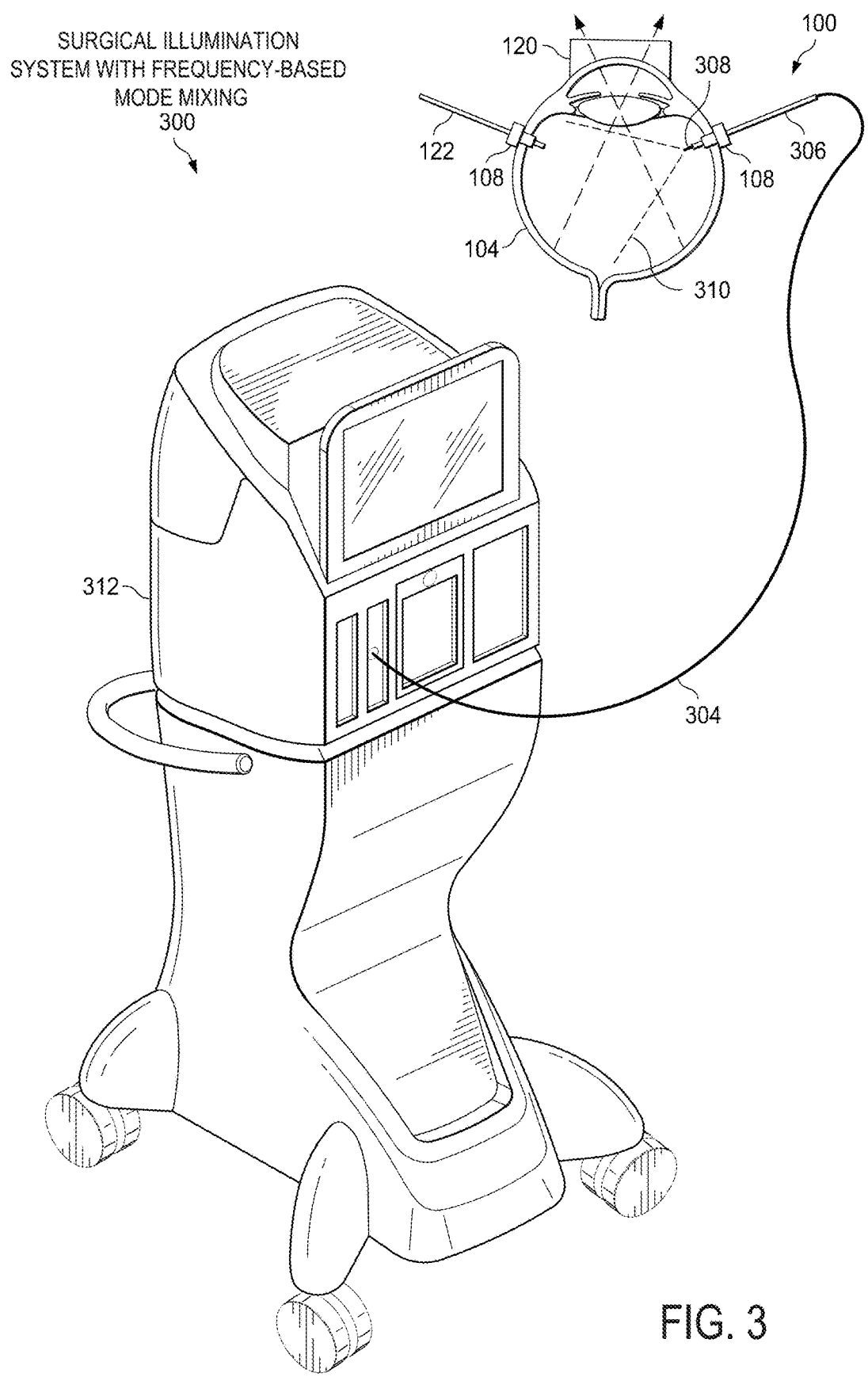
FIG. 3 is a depiction of an embodiment of a surgical illumination system with frequency-based mode mixing.

Referring now to FIG. 3, a depiction of an embodiment of a surgical illumination system 300 is shown. As shown in FIG. 3, surgical illumination system 300 may be used in the ophthalmic surgery on the eye 104 shown in FIG. 1. FIG. 3 is a schematic illustration and is not drawn to scale or perspective. In FIG. 3, a cross-sectional view of the eye 104 is shown, enabling a view of various elements described above with respect to FIG. 1. Specifically, contact lens 120 is shown providing a relatively wide angle view of the fundus of the eye 104, while two scleral ports 108 penetrate the sclera of the eye 104. A surgical tool 122 is shown penetrating one scleral port 108, while illumination assembly penetrates another scleral port 108.

As shown in FIG. 3, a homogeneous illumination field 310 is projected into the eye 104 by illuminator assembly 100. Specifically, illuminator assembly 100 terminates distally with an optical fiber portion 308, which may be exposed to project light into the eye. Optical fiber portion 308 is coupled to an external optical fiber 304. In some embodiments, optical fiber portion 308 may be a distal portion of external optical fiber 304 itself. Optical fiber 304 is shown passing through a hand piece 306, which may include a sheath or tube around optical fiber 304 to enable cannulation at scleral port 108. Optical fiber 304 is shown extending from a surgical console 312 to hand piece 306.

In FIG. 3, surgical console 312 may include frequency-based mixed mode surgical laser illumination, as disclosed herein. In some embodiments, the frequency-based mixed mode surgical laser illumination may be implemented as a separate device (see FIGS. 4B and 4C). Specifically, surgical console 312 may include a light source (see also FIG. 4A) comprised of a laser source, a laser modulator, and a condenser lens (or equivalent optical element). The laser modulator may modulate a frequency (or a wavelength) of first light generated by the laser source to generate second light that is frequency modulated. The condenser lens may focus the second light generated by the laser modulator onto a focal spot at a fiber core of optical fiber 304 at a proximal end. Because the frequency modulation creates or enhances mode mixing in optical fiber 304, the second light may provide a homogeneous illumination field 310 in the eye 104 after exiting optical fiber portion 308, which is at a distal end of optical fiber 304.

Surgical console 312 may provide various other equipment and functionality, such as driver equipment for surgical tool 122, and a user interface for data operations and image processing. Further internal details of the frequency-based mixed mode surgical laser illumination are described below with respect to FIGS. 4A, 4B, and 4C.

Figure 4A:
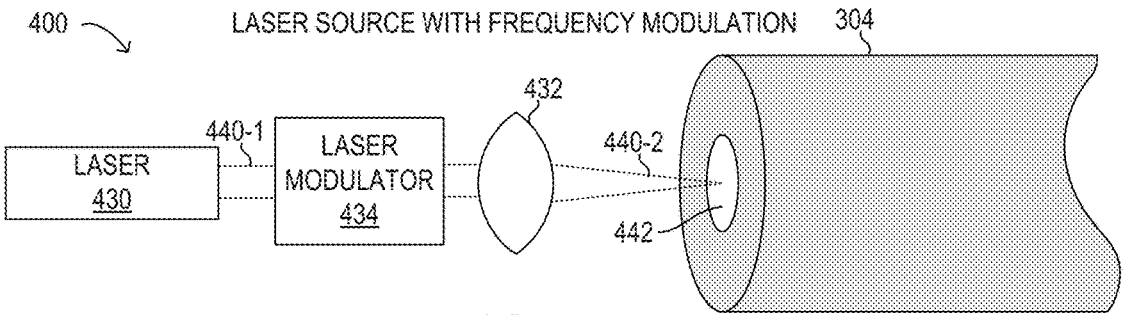
FIG. 4A is a depiction of an embodiment of a laser source with frequency modulation.

Referring now to FIG. 4A, a depiction of an embodiment of a laser source 400 with frequency modulation is shown. FIG. 4A is a schematic illustration and is not drawn to scale or perspective. In FIG. 4A, elements included within laser source 400 are shown schematically. It will be understood that laser source 400 may be implemented as an optical device, for example having an enclosure (not shown) to house the components illustrated in FIG. 4A. In particular embodiments, laser source 400 may be included with or integrated with surgical console 312 (see FIG. 3), where optical fiber 304 may begin at a distal end.

In laser source 400, a laser 430 may represent a source of coherent light. Laser 430 may represent a monochromatic light source. Laser 430 may represent a combination of a plurality of monochromatic light sources, in some embodiments. Laser 430 may generate first light 440-1, which is coherent light. First light 440-1 may be projected onto a laser modulator 434, which may be any of a variety of different types of laser modulators, such as, but not limited to an electro-optical modulator or a Mach-Zehnder modulator. Although laser modulator 434 may be enabled to modulate various properties of incoming light (first light 440-1), for the purposes of mode mixing disclosed herein laser modulator 434 may modulate a frequency of the incoming light. Laser modulator 434 may output frequency modulated laser light to a condenser lens 432, which may be used to focus first light 440-1 onto a fiber core 442 of optical fiber 304 to generate second light 440-2. First light 440-1 may be generated as a collimated laser beam of about 1-5 mm in diameter having an optical power in the range of about 10-500 mW in various embodiments. Second light 440-2 may be focused onto a focal spot that is about 5-10 μm in diameter by condenser lens 432. The focal spot may be less than 20 μm in diameter, or less than 25 μm in diameter in various embodiments. Fiber core 442 may be as small as about 30 μm in diameter. In some embodiments, fiber core 442 may about 50 μm in diameter, or about 100 μm in diameter, or various diameter sizes therebetween.

As shown in FIG. 4A, laser modulator 434 may be controlled to modulate a frequency of first light 440-1. The modulation frequency introduced by laser modulator 434 may be greater than what the human eye can perceive, or greater than about 30 Hz in various embodiments. The modulation amplitude introduced by laser modulator 434 may vary according to different criteria or parameters. For example, the modulation amplitude introduced by laser modulator 434 may be dependent upon certain characteristics of optical fiber 304 that receives second light 440-2 from laser modulator 434. For example, the modulation amplitude may be inversely related to a length of optical fiber 304, because shorter fibers will have shorter path lengths for homogeneous mode mixing. In another example, the modulation amplitude may be inversely related to a dispersion value of optical fiber 304, since greater dispersion results in increased homogeneity of light in an optical fiber. Other properties of optical fiber 304, such as a fiber core diameter, an index of refraction of the fiber core, and a numerical aperture of optical fiber 304 may also be used to determine the modulation amplitude introduced by laser modulator 434.

Figure 4B:
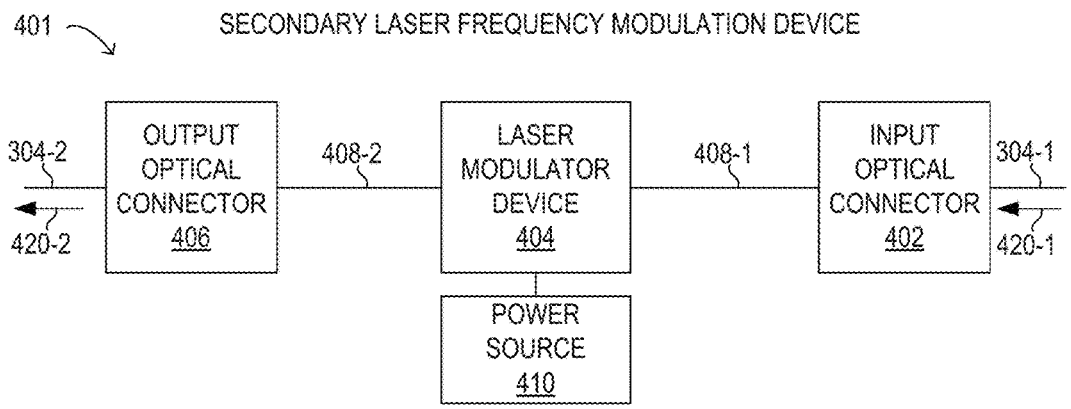
FIG. 4B is a depiction of an embodiment of a secondary laser frequency modulation device.

Referring now to FIG. 4B, a depiction of an embodiment of a secondary laser frequency modulation device 401 is shown. FIG. 4B is a schematic illustration and is not drawn to scale or perspective. In FIG. 4B, elements included within secondary laser frequency modulation device 401 are shown schematically. It will be understood that secondary laser frequency modulation device 401 may be implemented as an optical device, for example having an enclosure (not shown) to house the components illustrated in FIG. 4B. In particular embodiments, secondary laser frequency modulation device 401 may be installed along optical fiber 304 as an intermediate optical device, while optical fiber 304 may be implemented in two sections with the appropriate optical connectors.

Specifically, secondary laser frequency modulation device 401 is shown having input optical connector 402 for connecting to optical fiber 304-1, as well as having output optical connector 406 for connecting to optical fiber 304-2. In various embodiments, input optical connector 402 and output optical connector 406 may be releasable connectors (not shown) that mate with corresponding connectors attached to optical fibers 304-1 and 304-2. In some embodiments, input optical connector 402 and output optical connector 406 may be fixed connectors. As shown, input optical connector 402 couples to a first internal optical fiber 408-1 that connects to a laser modulator device 404. Laser modulator device 404 may connect to output optical connector 406 using a second internal optical fiber 408-2.

In secondary laser frequency modulation device 401, input optical connector 402 may receive first light 420-1, which may experience insufficient mode mixing in optical fiber 304-1 after being transmitted from a coherent light source. The coherent light source may be a monochromatic laser, or a combination of monochromatic lasers that have been combined to generate first light 420-1. Accordingly, first light 420-1 may include light from different frequencies (i.e., colors). First light 420-1 is transmitted by first internal optical fiber 408-1 to a laser modulator device 404, which is similar to laser source 400, and is described in further detail below with respect to FIG. 4C. Laser modulator device 404 may output second light 420-2 that has been mode mixed to second internal optical fiber 408-2, which connects to output optical connector 406.

Also shown with secondary laser frequency modulation device 401 in FIG. 4B is power source 410, which may provide power to laser modulator device 404. In some embodiments, power source 410 may represent an internal power source to secondary laser frequency modulation device 401, such as a battery to enable remote operation. In other embodiments, power source 410 may represent an external power source, such as a connector for line power or direct current from an external power supply (not shown).

Figure 4C:
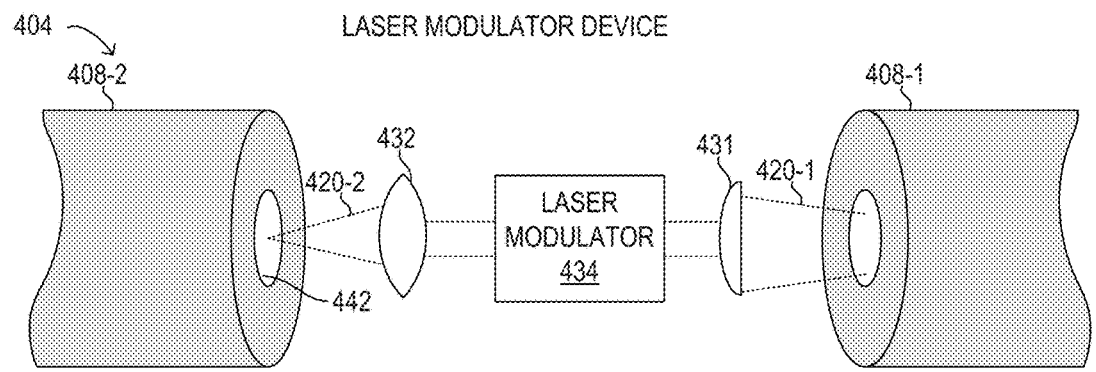
FIG. 4C is a depiction of an embodiment of a laser modulation device.

Referring now to FIG. 4C, a depiction of an embodiment of laser modulator device 404 (see also FIG. 4B) is shown. FIG. 4C is a schematic illustration and is not drawn to scale or perspective. In FIG. 4C, elements included within laser modulator device 404 are shown schematically. It will be understood that laser modulator device 404 may be implemented as an optical device, for example having an enclosure (not shown) to house the components illustrated in FIG. 4C. In particular embodiments, laser modulator device 404 may be included with secondary laser frequency modulation device 401 described above. As shown, laser modulator device 404 includes first internal optical fiber 408-1, second internal optical fiber 408-2, collimator lens 431, condenser lens 432, and laser modulator 434.

In laser modulator device 404, first light 420-1 arrives from first internal optical fiber 408-1, as described previously. First light 420-1 may be collimated into a parallel beam by collimator lens 431 and then projected onto laser modulator 434, which may be used to modulate a frequency of first light 420-1 to generate second light 420-2. Second light 420-2 exiting laser modulator 434 may be focused onto fiber core 442 by condenser lens 432. The operation of laser modulator 434 is described above with regard to FIG. 4A. Because of the frequency modulation, second light 420-2 may exhibit enhanced mode mixing and may be used to project homogeneous illumination field 310 for surgical illumination.

Figure 5:
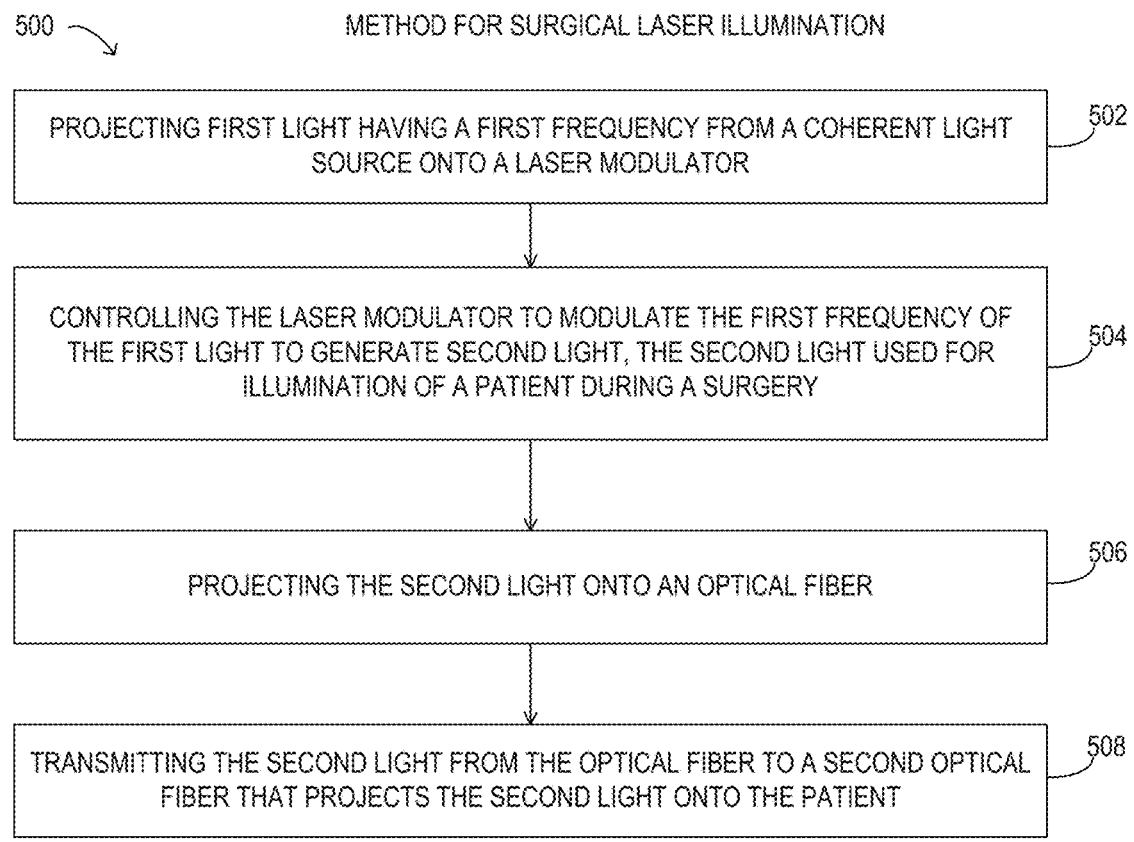
FIG. 5 is a flow chart of selected elements of a method for surgical laser illumination.

Referring now to FIG. 5, a flow chart of selected elements of an embodiment of a method 500 for surgical laser illumination using frequency-based mode mixing, as described herein, is depicted in flowchart form. It is noted that certain operations described in method 500 may be optional or may be rearranged in different embodiments. Method 500 may be performed using illumination assembly 100, along with laser source 400 or secondary laser frequency modulation device 401, as described herein.

Method 500 may begin, at step 502, by projecting first light having a first frequency from a coherent light source onto a laser modulator. At step 504, the laser modulator is controlled to modulate the first frequency of the first light to generate second light, the second light used for illumination of a patient during a surgery. At step 506, the second light is projected onto an optical fiber. At step 508, the second light is transmitted from the optical fiber to a second optical fiber that projects the second light onto the patient.

As disclosed herein, frequency-based mode mixing may be used to homogenize different modes in an optical fiber used for surgical illumination. A laser modulator may introduce frequency modulation to laser light to generate a homogeneous illumination field due to increased mode mixing in the optical fiber.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for ophthalmic surgical illumination, the method comprising:
    projecting first light having a first frequency from a coherent light source onto a laser modulator;
    controlling the laser modulator to modulate the first frequency of the first light to generate second light, the second light used for illumination of a patient during a surgery;
    projecting the second light onto an optical fiber; and
    transmitting the second light from the optical fiber into an eye of the patient;
    wherein the coherent light source is a laser, and wherein the laser modulator is included in a laser modulator device further comprising:
    an input for receiving the first light;
    an output optical connector for connection to the optical fiber; and
    a power source to power the laser modulator.

2. The method of claim 1, wherein controlling the laser modulator further comprises:
    controlling a modulation amplitude to modulate the first frequency of the first light.

3. The method of claim 2, wherein controlling the laser modulator further comprises:
    controlling the modulation amplitude based on a transmission characteristic of the optical fiber.

4. The method of claim 3, wherein the transmission characteristic of the optical fiber is selected from at least one of:
    a length of the optical fiber;
    a dispersion value for the optical fiber;
    a core diameter of a core of the optical fiber; and
    an index of refraction of the core of the optical fiber.

5. The method of claim 1, wherein the coherent light source is a monochromatic laser.

6. The method of claim 1, wherein projecting the second light onto the optical fiber further comprises:
    projecting the second light onto the optical fiber using a condenser lens.

7. The method of claim 1, wherein a modulation frequency to modulate the first frequency of the first light is at least 30 Hertz (Hz).

8. The method of claim 1, wherein transmitting the second light from the optical fiber into the eye of the patient comprises transmitting the second light through a second optical fiber that projects the second light onto the eye of the patient;
    wherein the coherent light source further comprises a third optical fiber receiving the first light from the laser, and wherein the laser modulator device further comprises:
    an input optical connector for connection to the third optical fiber.

9. A device for ophthalmic surgical illumination, the device comprising:
    a coherent light source for generating first light having a first frequency for illumination of a patient during a surgery;
    a laser modulator for receiving the first light and for modulating the first frequency of the first light to generate second light;
    an optical fiber for receiving the second light; and
    wherein the coherent light source is a laser, and wherein the laser modulator is included in a laser modulator device further comprising:
    an input for receiving the first light;
    an output optical connector for connection to the optical fiber; and
    a power source to power the laser modulator.

10. The device of claim 9, wherein the laser modulator is controlled by:
    controlling a modulation amplitude to modulate the first frequency of the first light.

11. The device of claim 9, wherein the laser modulator is controlled by:
    controlling the modulation amplitude based on a transmission characteristic of the optical fiber.

12. The device of claim 11 wherein the transmission characteristic of the optical fiber is selected from at least one of:
    a length of the optical fiber;
    a dispersion value for the optical fiber;
    a core diameter of a core of the optical fiber; and
    an index of refraction of the core of the optical fiber.

13. The device of claim 9, wherein the coherent light source is a monochromatic laser.

14. The device of claim 9, further comprising:
    a condenser lens for projecting the second light onto the optical fiber.

15. The device of claim 9, wherein a modulation frequency to modulate the first frequency of the first light is at least 30 Hz.

16. The device of claim 9, further comprising a second optical fiber receiving the second light from the optical fiber, the second optical fiber projecting the second light onto the patient and
    wherein the coherent light source further comprises a third optical fiber receiving the first light from the laser, and wherein the laser modulator device further comprises:
    an input optical connector for connection to the third optical fiber.

* * * * *